(12) United States Patent
Abelli et al.

(10) Patent No.: US 9,522,204 B2
(45) Date of Patent: *Dec. 20, 2016

(54) TREATMENT APPARATUS, USING A STERILIZING SUBSTANCE, FOR CLOSURES FOR CONTAINERS

(71) Applicant: GEA PROCOMAC S.P.A., Sala Baganza (IT)

(72) Inventors: Paolo Abelli, Parma (IT); Fabio Callegari, Salsomaggiore Terme (IT)

(73) Assignee: GEA PROCOMAC S.P.A., Sala Baganza (IT)

( * ) Notice: Subject to any disclaimer, the term of this patent is extended or adjusted under 35 U.S.C. 154(b) by 0 days.

This patent is subject to a terminal disclaimer.

(21) Appl. No.: 14/762,154

(22) PCT Filed: Jan. 30, 2014

(86) PCT No.: PCT/IB2014/058675
§ 371 (c)(1),
(2) Date: Jul. 20, 2015

(87) PCT Pub. No.: WO2014/140949
PCT Pub. Date: Sep. 18, 2014

(65) Prior Publication Data
US 2015/0367010 A1  Dec. 24, 2015

(30) Foreign Application Priority Data

Mar. 11, 2013  (IT) .............................. PR2013A0017

(51) Int. Cl.
*A61L 2/22* (2006.01)
*B67B 3/00* (2006.01)

(52) U.S. Cl.
CPC . *A61L 2/22* (2013.01); *B67B 3/00* (2013.01); *B67B 3/003* (2013.01); *A61L 2202/23* (2013.01)

(58) Field of Classification Search
CPC .............. A61L 2/22; B67B 3/00; B67B 3/003
See application file for complete search history.

(56) References Cited

U.S. PATENT DOCUMENTS

| 5,123,229 | A | * | 6/1992 | Dardaine | .............. B65B 55/025 198/468.2 |
|---|---|---|---|---|---|
| 7,360,345 | B2 | | 4/2008 | Topf | |
| 2007/0157552 | A1 | | 7/2007 | Cirio | |

(Continued)

FOREIGN PATENT DOCUMENTS

| DE | 10 2010 052 207 A1 | 5/2012 |
|---|---|---|
| EP | 1 801 066 A2 | 6/2007 |

(Continued)

*Primary Examiner* — Regina M Yoo
(74) *Attorney, Agent, or Firm* — Pearne & Gordon LLP (57) ABSTRACT

A treatment apparatus (1) of closures (2, 22) for containers using a sterilizing substances, comprising: a rotating unit (6); dispensing means (16) of the sterilizing substance; at least two types of rails (7a, 7b), longitudinal and parallel, of which a first type of rails (7a) houses, by force of gravity, a first format of closures (2) and a second type of rails (7b) houses, by force of gravity, a second format of closures (22), the rails (7a, 7b) being solidly constrained to the rotating unit (6) and being arranged in such a way as to follow a circumferential extension thereof.

12 Claims, 11 Drawing Sheets

(56) References Cited

U.S. PATENT DOCUMENTS

| | | | |
|---|---|---|---|
| 2010/0170867 A1* | 7/2010 | Hayakawa | B67C 7/0073 |
| | | | 215/379 |
| 2011/0142731 A1* | 6/2011 | Beckmann | A61L 2/208 |
| | | | 422/292 |
| 2013/0052089 A1 | 2/2013 | Drenguis | |
| 2013/0193344 A1 | 8/2013 | Drenguis | |
| 2015/0246801 A1* | 9/2015 | Niehr | A61L 2/20 |
| | | | 422/28 |

FOREIGN PATENT DOCUMENTS

| | | |
|---|---|---|
| EP | 2 246 176 A1 | 11/2010 |
| EP | 2039439 A1 | 12/2010 |
| EP | 2 279 850 A1 | 2/2011 |
| WO | 2010/031464 A2 | 3/2010 |
| WO | 2012/000573 A1 | 1/2012 |

* cited by examiner

TREATMENT APPARATUS, USING A STERILIZING SUBSTANCE, FOR CLOSURES FOR CONTAINERS

TECHNICAL FIELD

The present invention relates to a treatment apparatus for closures for containers using a sterilizing substance. In particular, the apparatus of the invention is applicable to the field of bottling using aseptic technology.

STATE OF THE ART

As is known, in a bottling line with aseptic technology, contamination control in the various work stations (forming, filling, capping, etc.) is of primary importance; for this reason it is essential to ensure an adequate filtering of the fluids to be placed inside the controlled environment, proper management of the pressures of the various areas so as to control the path of any unwanted particles, correct monitoring of the environment, proper management and adequate quality of CIP ("Cleaning In Place") and S.I.P. sterilization ("Sterilization In Place") cycles.

The Applicant has recently developed an isolating apparatus able to define a contamination-controlled environment housing the various work stations of a bottling line, such as sterilization of the preforms, container forming, filling of the formed containers and closing the filled containers. The apparatus and the method therefor are described in detail in European Patent EP2246176 and in European patent application EP2279850 in the name of the present Applicant.

In an aseptic bottling line, before the filling of the formed containers and the capping thereof, there is also a need to sterilize the closures (caps or capsules) of the containers themselves, for example using chemical agents or using energy sources. The invention disclosed herein relates to sterilization using chemical agents. In this context, various solutions are known, such as for example:

- an apparatus for sterilising caps internally of a rotating transport system, described in document WO201003146;
- an immersion sterilising system of capsules along a spiral path, described in document EP2039439;
- a sterilising drum containing a plurality of rotating discs supporting the capsules, described in document U.S. Pat. No. 7,360,345;
- a system formed by two superposed rotors for carrying out the treatment in three steps (pre-heating, dosing and activation of the sterilising substance), described in document WO2012000573.

These prior-art solutions enable treating closures having a predetermined format, using complex change-format operations whenever the apparatus/system has to treat caps or capsules having different formats. The change-format operations often require replacement of various components (for example discs, receptacles for supporting the caps, chutes etc.) and therefore require shutting down the machine for relatively long times.

OBJECT OF THE INVENTION

In this context, the technical objective underpinning the present invention is to provide a treatment apparatus of closures for containers with a sterilizing substance, which obviates the drawbacks of the above-mentioned prior art.

In particular, the aim of the present invention is to disclose a treatment apparatus of closures for containers by means of a sterilizing substance which can operate on closures of different formats thus avoiding complex change-format operations and reduce and/or eliminate the times required for the format change.

A further aim of the present invention is to make available a treatment apparatus of closures for containers using a sterilizing substance which apparatus is compact, structurally simple and, at the same time, more effective than the known solutions.

The set technical objective and the aims specified are substantially attained by a treatment apparatus of closures for containers with a sterilizing substance, comprising the technical characteristics set out in one or more of the appended claims.

BRIEF DESCRIPTION OF THE DRAWINGS

Further characteristics and advantages of the present invention will more fully emerge from the description given by way of non-limiting example of a preferred but not exclusive embodiment of a treatment apparatus of closures for containers with a sterilizing substance, as illustrated in the appended drawings, in which:

FIGS. 6a, 6b and 6c illustrate three embodiments of the support profile of the treatment apparatus of FIG. 1, in a perspective view;

DETAILED DESCRIPTION OF PREFERRED EMBODIMENTS OF THE INVENTION

With reference to the figures, reference numeral 1 denotes a treatment apparatus of closures 2, 22 for containers using a sterilizing substance. For example, the sterilizing substance is hydrogen peroxide. In particular, the sterilizing substance is gaseous. Alternatively, the sterilizing substance is liquid.

In this context, the term closure 2, 22 relates to a concave closure such as a cap or a capsule. The closure 2, 22 is preferably made of a polymer material.

Figure 7A:
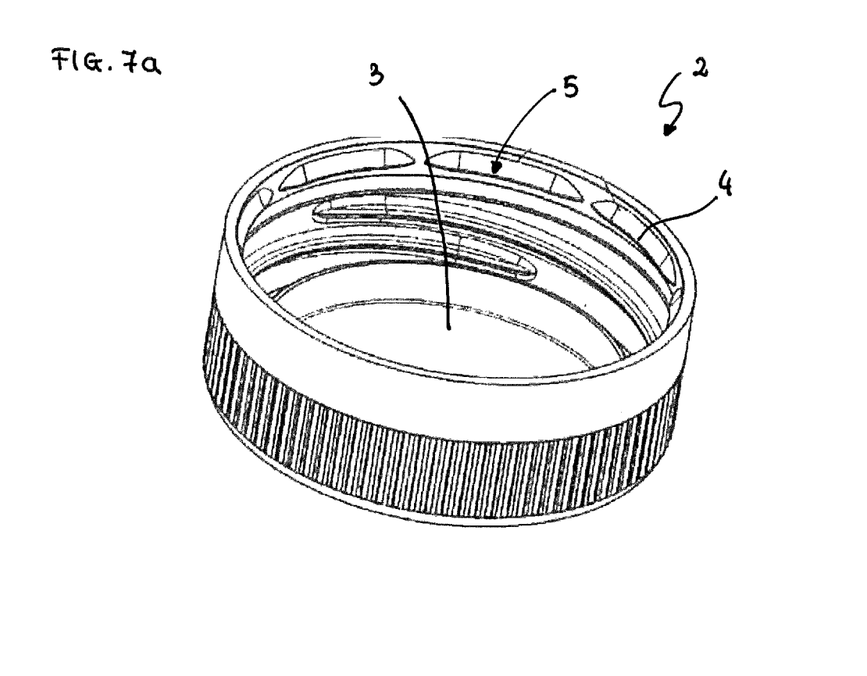
FIGS. 7a and 7b illustrate two different closures, respectively a flat cap and a sport cap, in perspective views.

FIG. 7a illustrates a first closure 2 format; this is known as a flat cap.

Figure 7B:
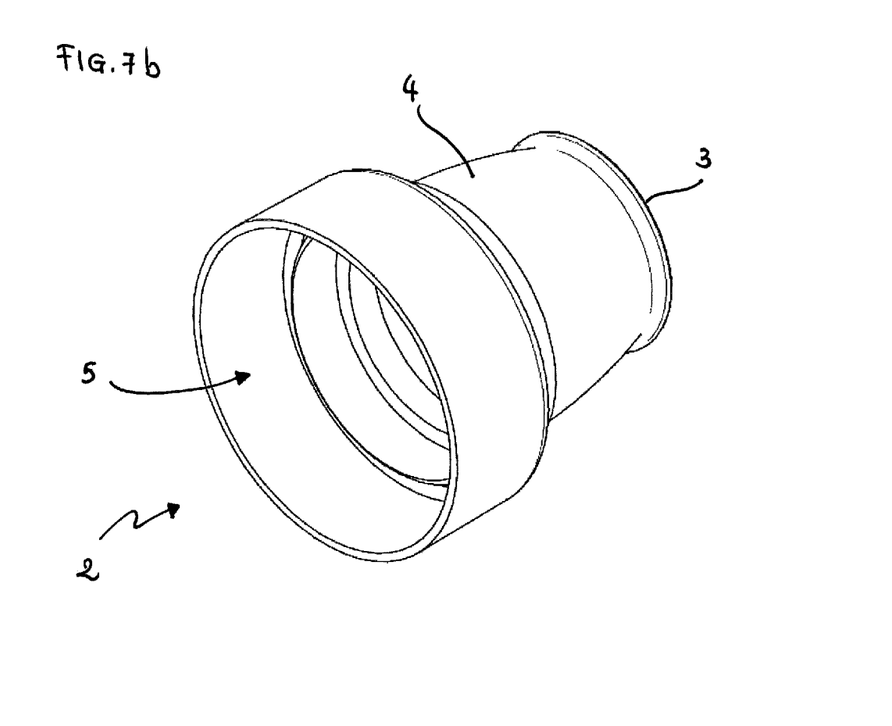
Figure 8:
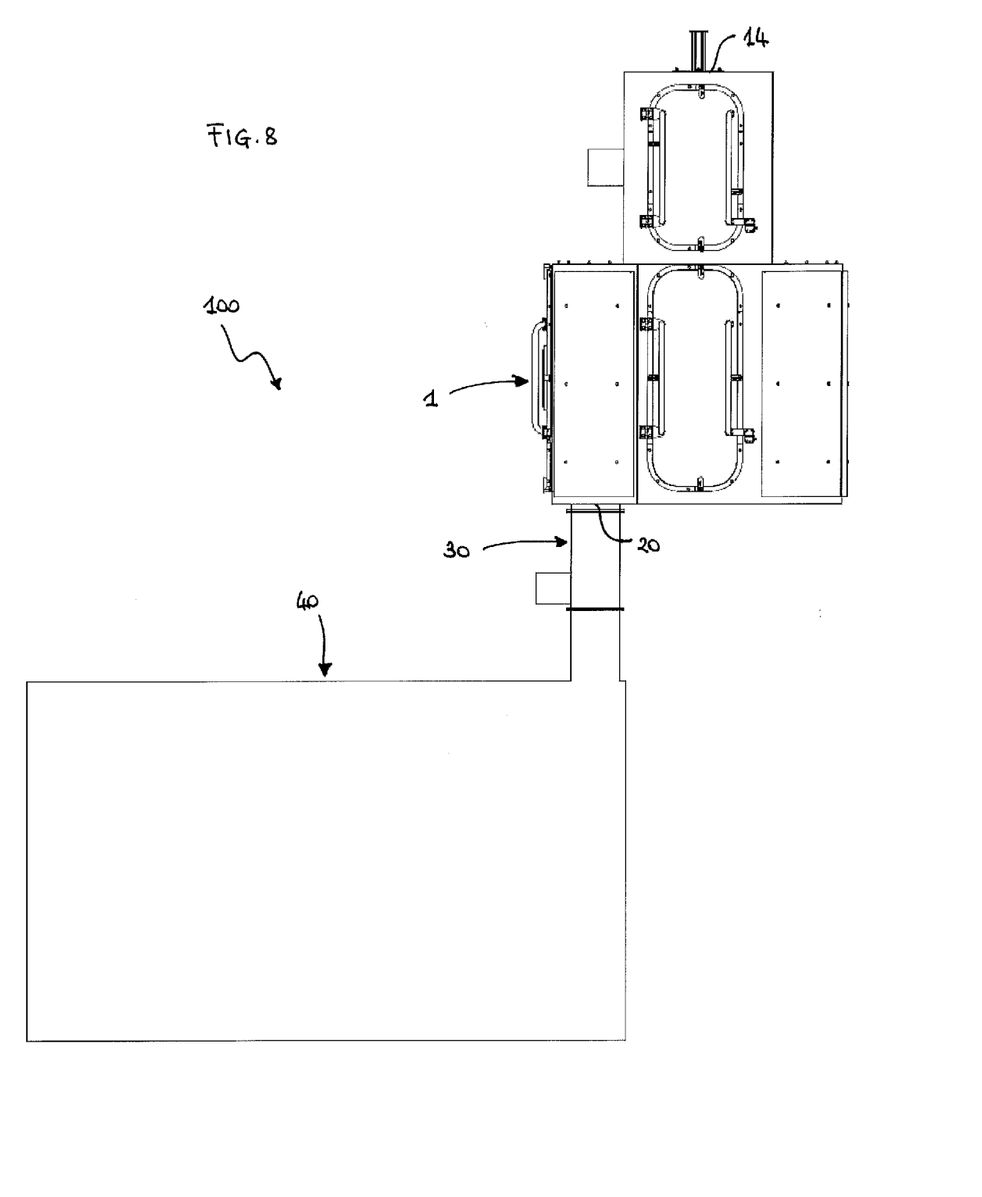
FIG. 8 illustrates a schematic view of a bottling line comprising the treatment apparatus of FIG. 1.

FIG. 7b illustrates a second closure forma 22; this is known as a sport cap.

In both cases, the closure 2, 22 has a base 3 and a lateral wall 4 extending from the base 3 and defining therewith a cavity 5. The cavity 5 is open: in fact, on the side opposite the base 3 the closure 2, 22 has an opening that can accommodate the mouth of a container so that the lateral wall 4 can engage therewith and the base 3 can close it.

In this context, the term "internal surfaces" of the closure 2, 22 identifies the internal surface of the lateral wall 4 and the internal surface of the base 3. The term "external surfaces" of the closure 2, 22 refers to the external surface of the lateral wall 4 and the external surface of the base 3.

In FIG. 7a the cavity 5 delimited by the flat cap 2 exhibits a substantially cylindrical shape, so that the lateral wall 4 corresponds substantially to the lateral wall of a cylinder and the base 3 is a circular disc. Alternatively, the cavity 5 delimited by the closure 2 has a slightly conical shape.

The sport cap 22 of FIG. 7b exhibits a more complex shape, though the base 3, the lateral wall 4 and the cavity 5 can also be identified therein.

The treatment apparatus 1 comprises a rotating unit 6 and a plurality of longitudinal rails 7a, 7b able to house the closures 2, 22 arranged by force of gravity in a same number of lines 8. The rails 7a, 7b are substantially parallel to one another and are solidly connected to the rotating unit 6 in such a way as to follow the circumferential extension thereof.

The rails 7a, 7b are originally of at least two types. The rails 7a of a first type are conformed so as to house the closures 2 of the first format. The rails 7b of a second type are conformed in such a way as to house the closures 22 of the second format. In the embodiment described and illustrated herein, each rail 7a of the first type alternates with a rail 7b of the second type along the circumferential extension of the rotating unit 6.

An alternative embodiment (not illustrated) includes alternation of groups of rails 7a of the first type with groups of rails 7b of the second type along the circumferential extension of the rotating unit 6.

The rails 7a of the first type are preferably conformed in such a way as to house the flat caps 2. The rails 7b of the second type are preferably conformed in such a way as to house the sport caps 22.

In the embodiment described herein and illustrated, the rails 7a, 7b are of two types, but also possible are rails of three or more types, alternated with one another or in groups along the circumferential extension of the rotating unit 6.

In the embodiment described and illustrated herein, the rails 7a, 7b are parallel to the rotation axis A of the rotating unit 6.

In all the accompanying figures the treatment apparatus 1 is positioned on a support plane (ground or floor) in such a way that the rotation axis A of the rotating unit 6 is perpendicular to the support plane. Therefore, the rails 7a, 7b are also perpendicular to the support plane (as they are parallel to the rotation axis A).

There is also the possibility (not illustrated) of arranging the treatment apparatus 1 with the rotation axis A inclined with respect to the support plane. In this case, the rails 7a, 7b are also inclined with respect to the support plane (as they are parallel to the rotation axis A).

In an alternative embodiment (not illustrated), the rails 7a, 7b are inclined by a predetermined angle relative to the rotation axis A of the rotating unit 6.

The treatment apparatus 1 comprises a protection casing 9 able to define and isolate a controlled-contamination internal environment 10. For example, the protection casing 9 defines an internal environment 10 substantially in the shape of an octagonal prism or having a cylindrical shape.

In particular, the protection casing 9 comprises heating means for the walls of the casing 9 itself, which are in contact with the controlled-contamination internal environment 10. The heating means include means for controlling the temperature of the walls in order to avoid condensation.

The heating means are made in known ways.

The protection casing 9 is provided with at least an access window 11 enabling interventions for regulating and/or maintenance of the internal controlled-contamination environment 10. In the embodiment described and illustrated herein, there are three access windows 11 closable by means of corresponding airtight hatch doors 12.

Figure 4A:
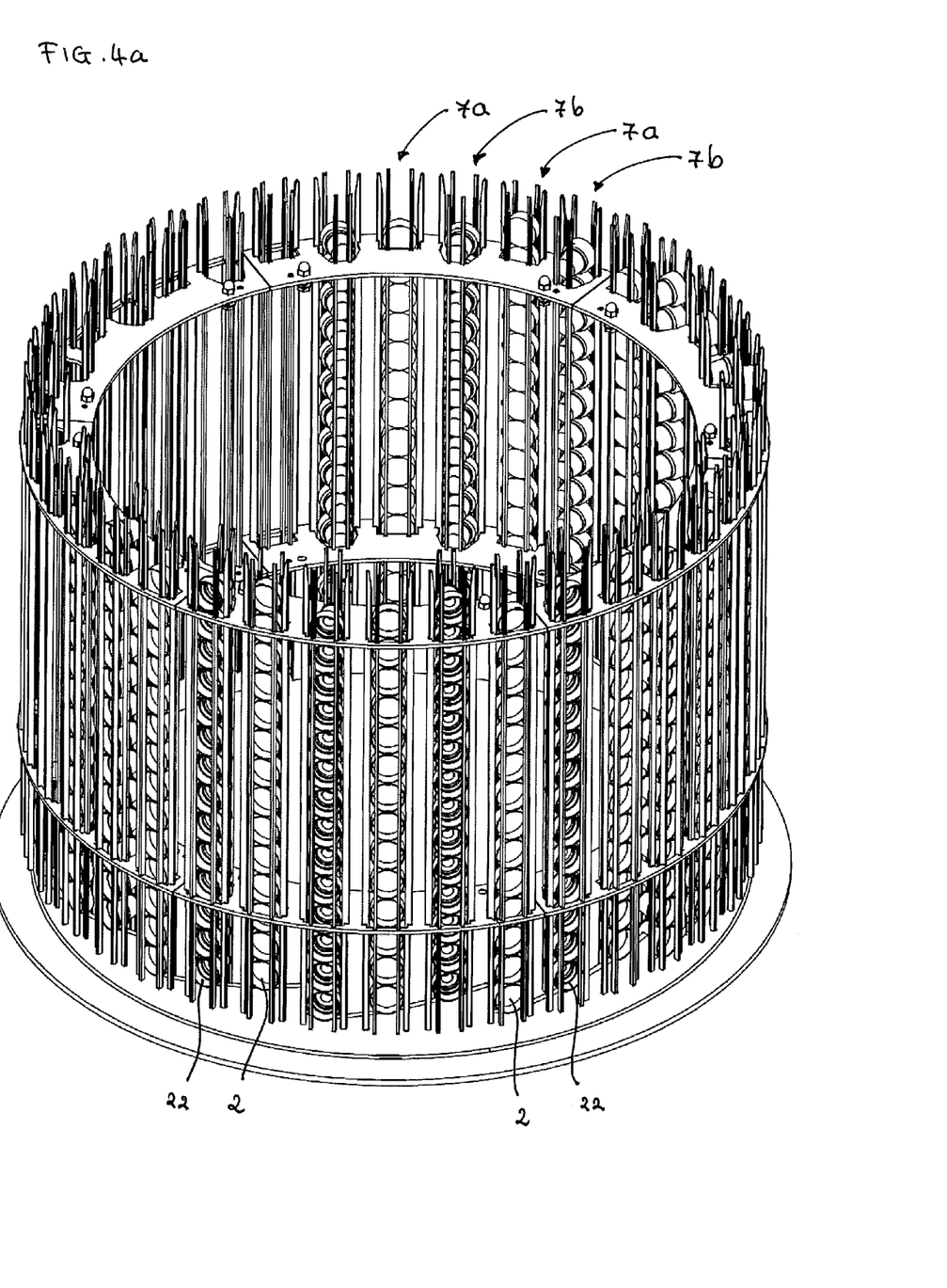
FIGS. 4a and 4b illustrate a portion of the treatment apparatus of FIG. 1 (rail, support profile), respectively in a perspective view and in a plan view.
Figure 4B:
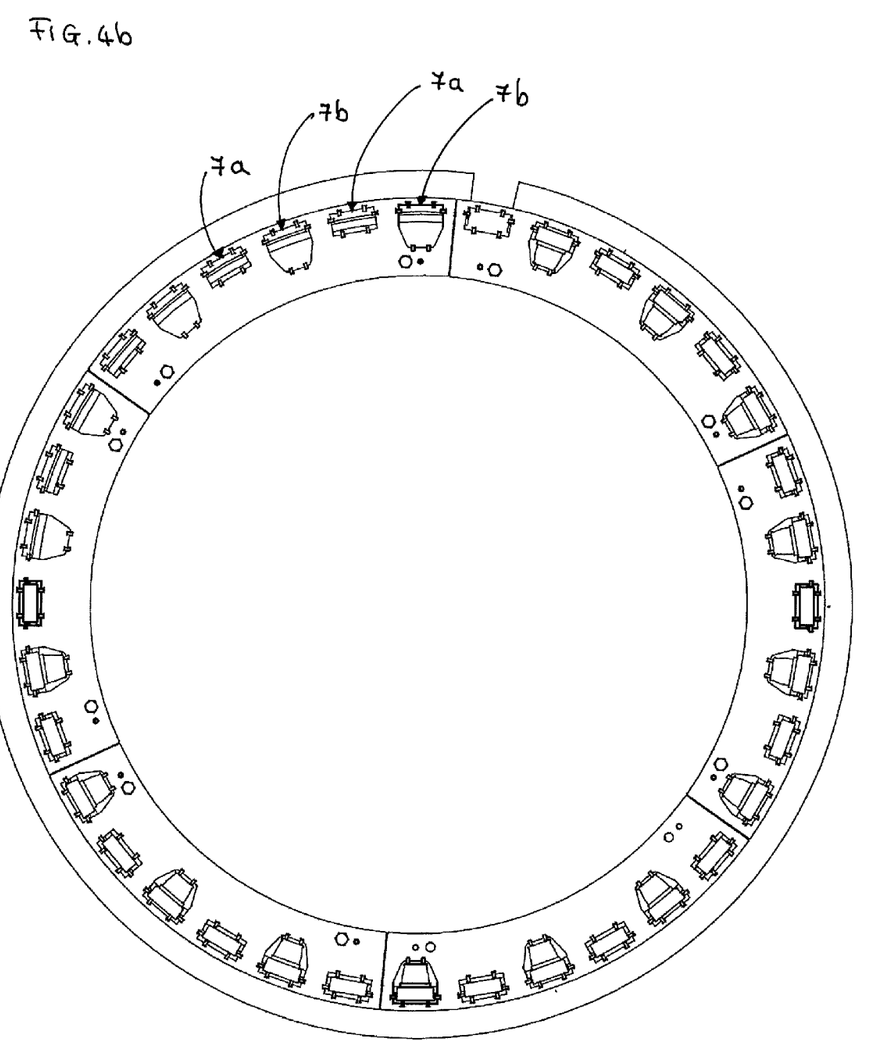

Each closure 2, 22 housed in the rails 7a, 7b exhibits the cavity 5 (and therefore the opening) facing outwards (see for example FIG. 4). In other words, the cavity 5 (and therefore the opening) is facing towards the protection casing 9.

The treatment apparatus 1 is preferably provided with conveying means 13 of the closures 2, 22 towards the internal controlled-contamination environment 10. The conveying means 13 comprise at least a first channel 13a on which the closures 2 of the first format advance by force of gravity, and a second channel 13b on which the closures 22 of the second format advance by force of gravity. The first channel 13a and the second channel 13b are preferably substantially vertical. Alternatively, the first channel 13a and the second channel 13b are inclined.

The protection casing 9 preferably exhibits an upper base 9a in which an opening 14 is afforded for access, into which the first channel 13a and the second channel 13b open.

The treatment apparatus 1 further comprises selecting means of the format (not illustrated), which are operatively active on the conveying means 13 so as to enable the supply of the first channel 13a or the second channel 13b.

The treatment apparatus 1 comprises a support profile 15 located below the rails 7a, 7b and also having a circumferential extension for supporting the lines 8 of closures 2, 22.

In the embodiment described and illustrated herein, the support profile 15 is fixed with respect to the rotating unit 6. In an alternative embodiment (not shown), the support profile 15 is mobile with respect to the rotating unit 6.

The support profile 15 has a variable height in such a way that, with the rotating unit 6 in rotation, the lines 8 of closures 2, 22 follow a circumferential path with level differences that can determine the relative displacements between the closures 2, 22.

The level differences circumferential path comprises at least a rising section 18 and at least a descending section 19. In the embodiments described and illustrated herein, the circumferential path with level differences comprises a plurality of rising sections 18 and a plurality of descending sections 19. For example, the rising sections 18 and descending sections 19 are ramps having a predetermined inclination, or are steps.

The treatment apparatus 1 comprises dispensing means 16 of the sterilizing substance. In the embodiment described and illustrated herein, the dispensing means 16 are fixed in relation to the rotating unit 6. Alternatively, the dispensing means 16 are mobile.

Figure 1:
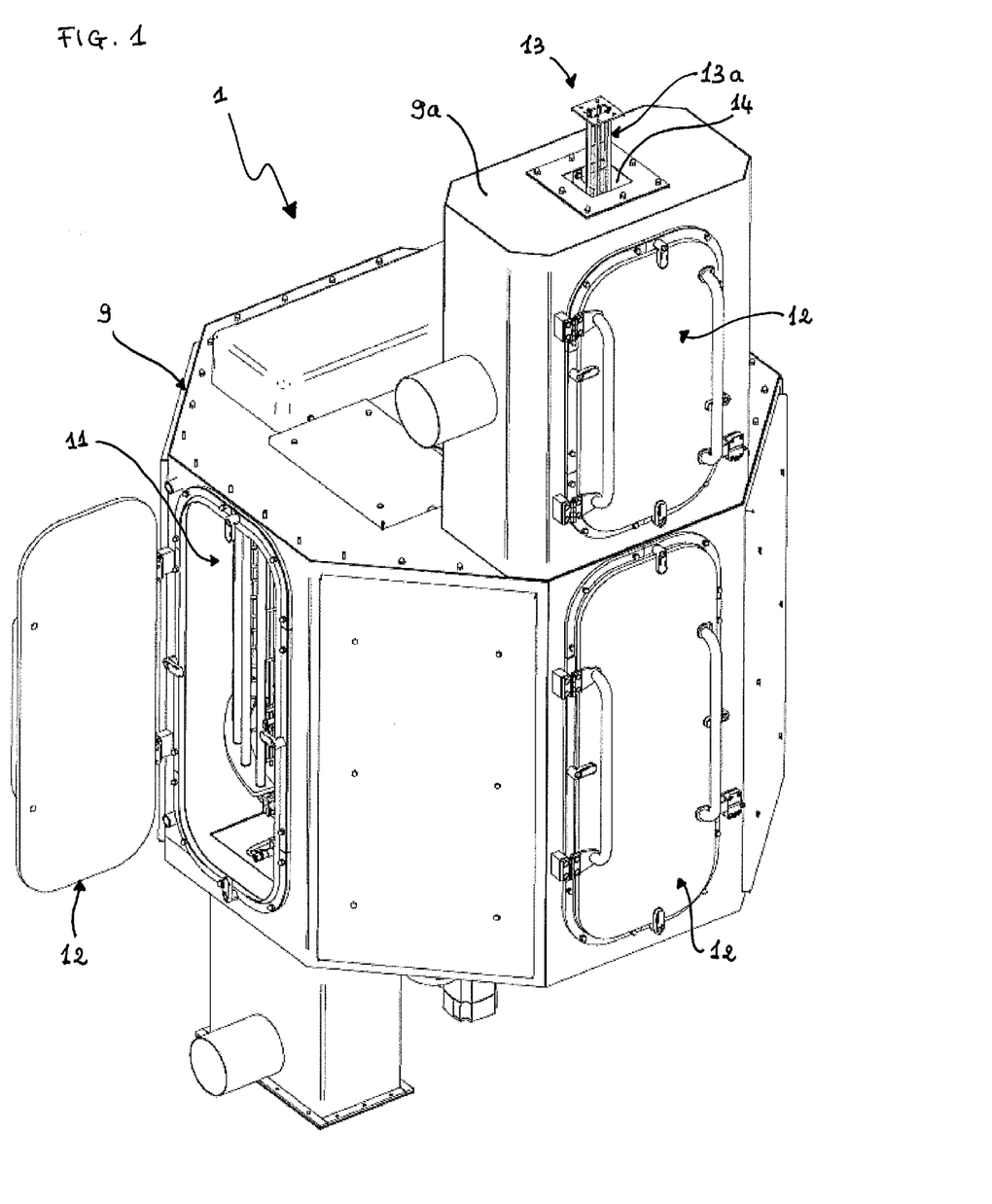
FIG. 1 illustrates a treatment apparatus of closures for containers with a sterilizing substance, in a perspective view from above.
Figure 2:
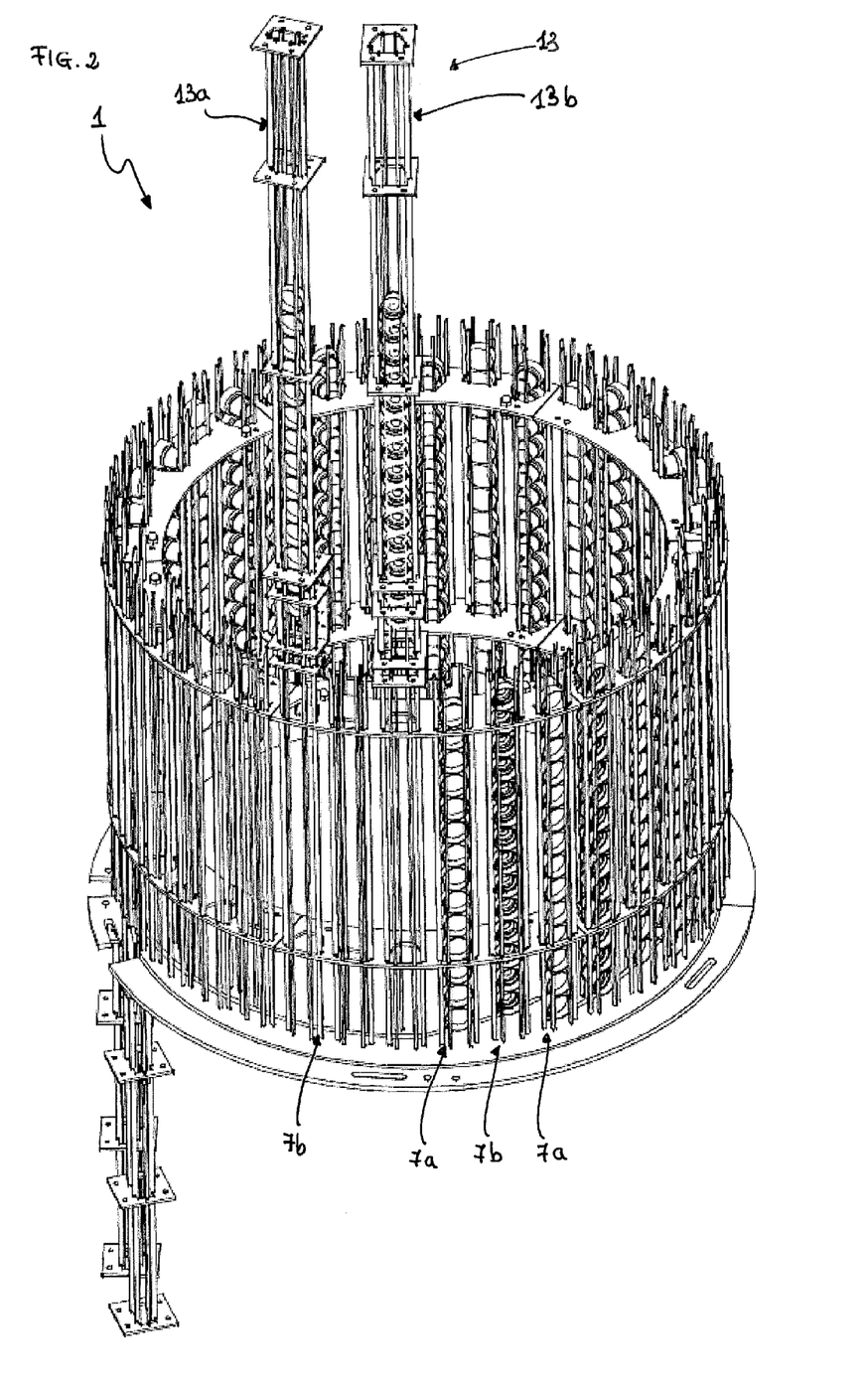
FIG. 2 illustrates the treatment apparatus of FIG. 1 (in which the protection casing has been partially removed), in a frontal perspective view.
Figure 3:
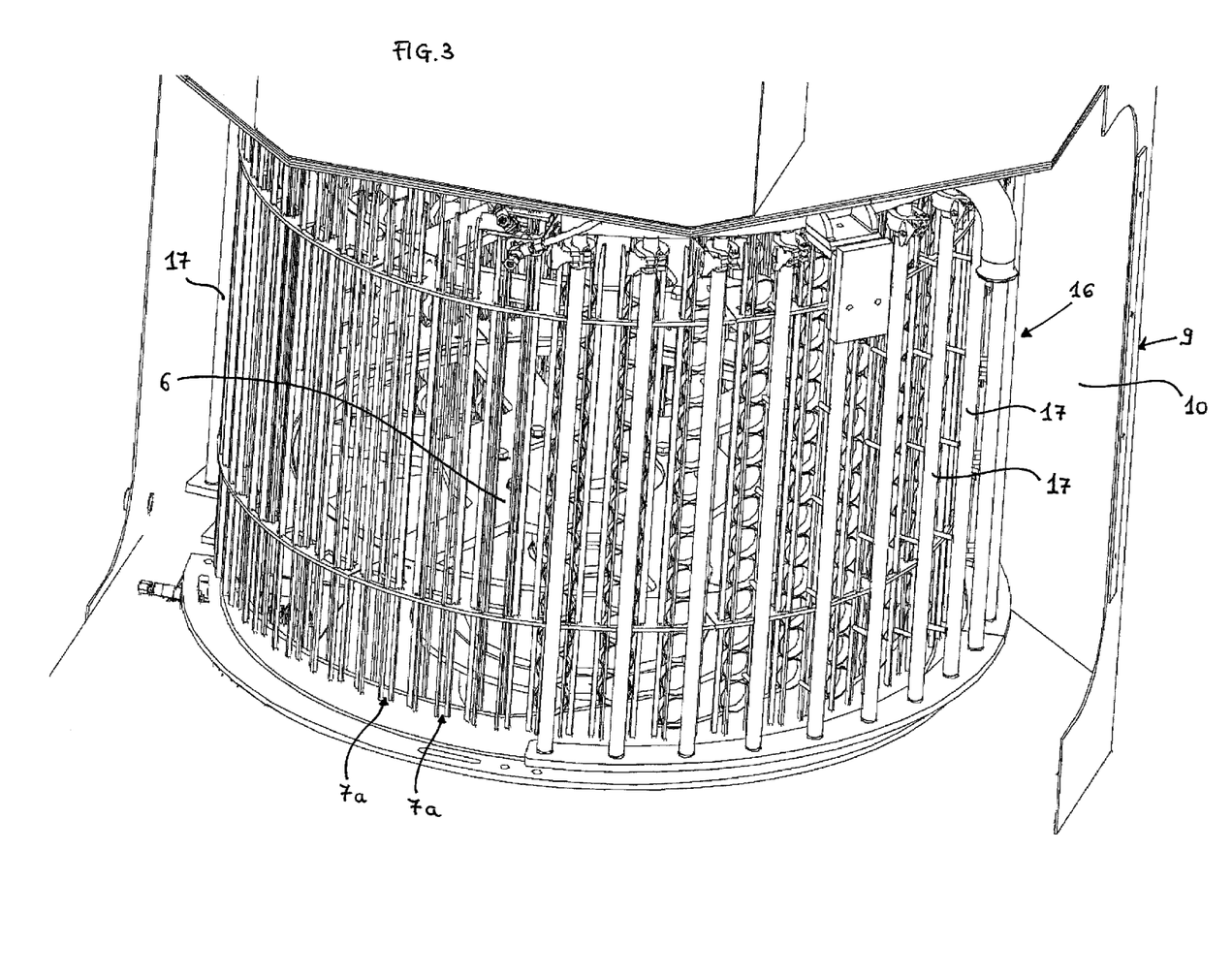
FIG. 3 illustrates a portion of the treatment apparatus of FIG. 1 (rotating unit, rails, dispensing means), in a perspective view.

In particular, the dispensing means 16 comprise a plurality of nozzles arranged in such a way as to deliver the sterilizing substance towards the cavities 5 of the closures 2, 22. In particular, the nozzles are positioned between the rails 7a, 7b and the protection casing 9 and therefore they also follow a circumferential extension. In other words, the dispensing means 16 define a concentric circumferential extension with a larger diameter than the circumferential extension of the housing rails 7a, 7b of the closures 2, 22 (see FIG. 3). In the embodiment described and illustrated herein the dispensing means 16 consist of tubular bodies 17 arranged substantially vertically, i.e. parallel to the rails 7a, 7b. Each of these tubular bodies 17 exhibits a plurality of nozzles.

The functioning of the treatment apparatus of closures for containers with a sterilizing substance, according to the present invention, will be described in the following.

Consider the rotating unit 6 initially in a stationary state. The selector means of the format enable for example supply of the first channel 13a.

The closures 2 of the first format (flat caps) advance by force of gravity in the first conveyor channel 13a and, when passing through the access opening 14, are arranged in the rail 7a of the first type positioned immediately below the access opening 14, thereby forming a first line 8. As mentioned above, each closure 2 is arranged with the cavity 5 facing the protection casing 9.

Figure 5A:
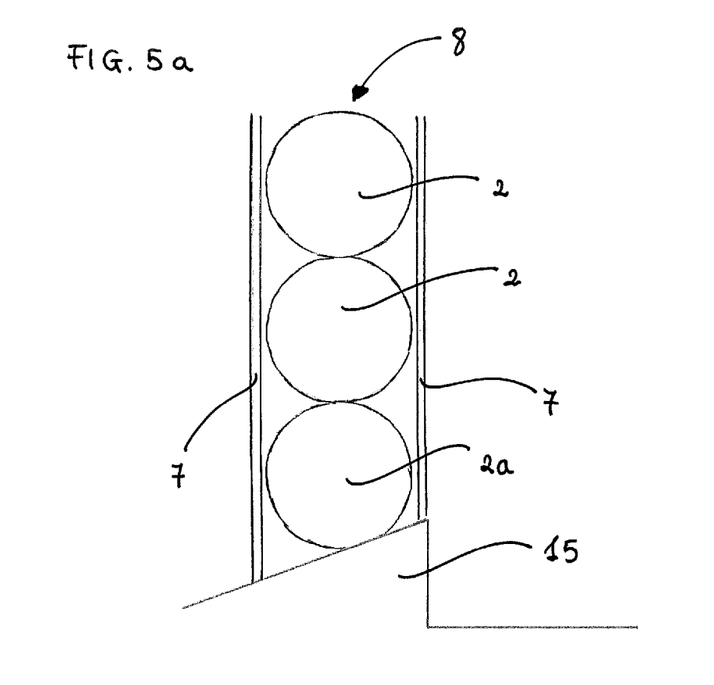
FIGS. 5a and 5b schematically illustrate the relative position of a line of closures with respect to the support profile at two different instants of rotation of the rotating unit.

The closure 2a of the line 8 which is located at a lower level (which for the sake of clarity we will call the head closure 2) rests on the support profile 15, as shown in FIG. 5a.

During the rotation of the rotating unit 6, the rails 7a, 7b rotate solidly with the rotating unit 6 and the closures 2 in arrival from the first conveyor channel 13a are unloaded one after another into the rail 7a of the first type positioned below the access opening 14. The selector means of the format further guarantee that the closures 2 of the first format are unloaded only into rails 7a of the first type.

Figure 5B:
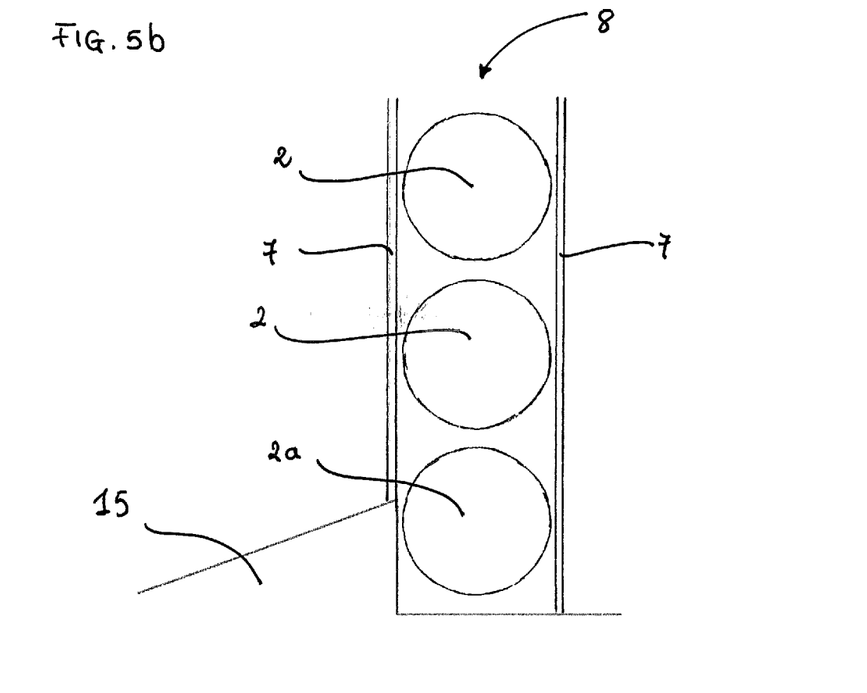
Figure 6A:
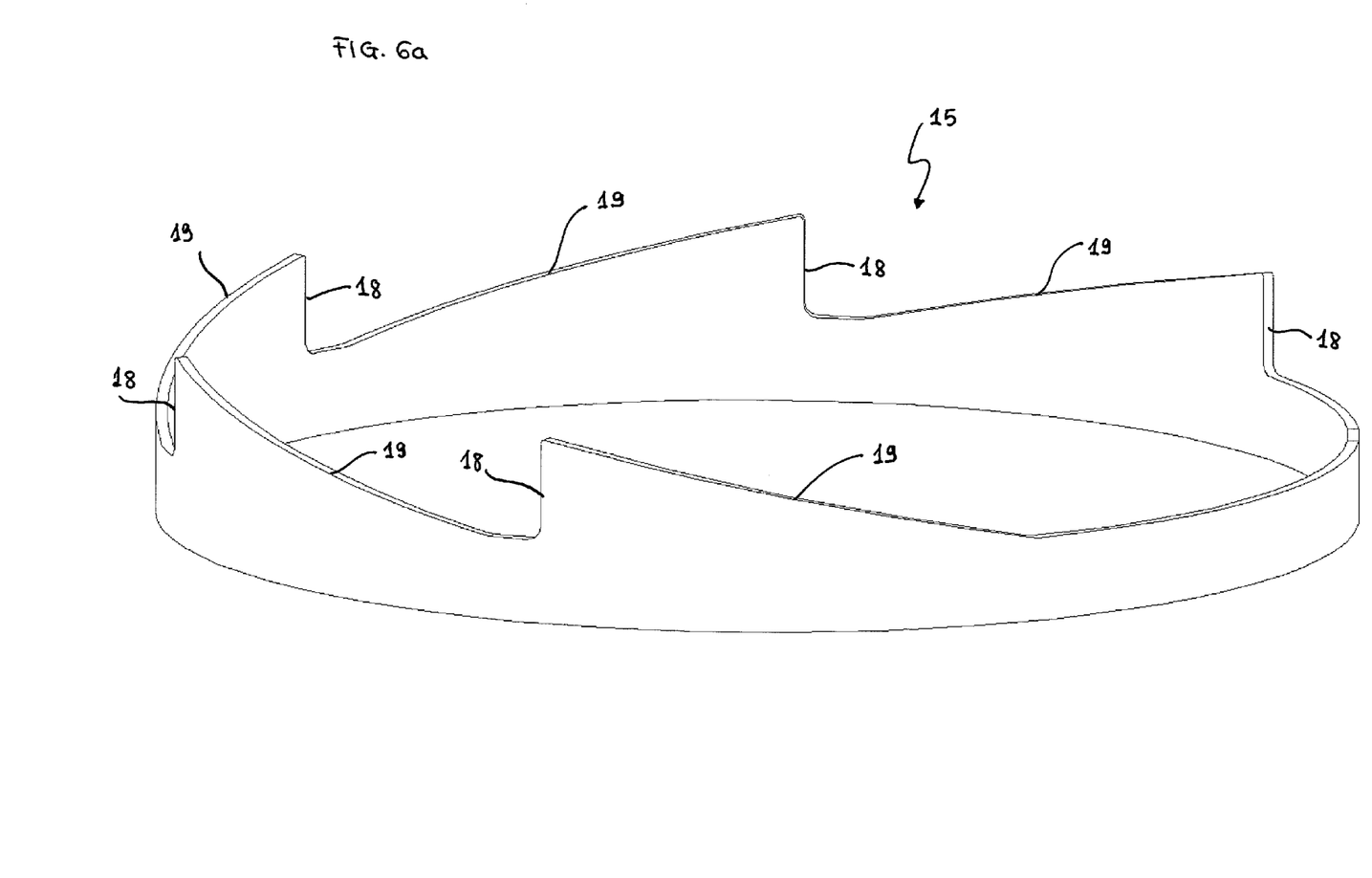
Figure 6C:
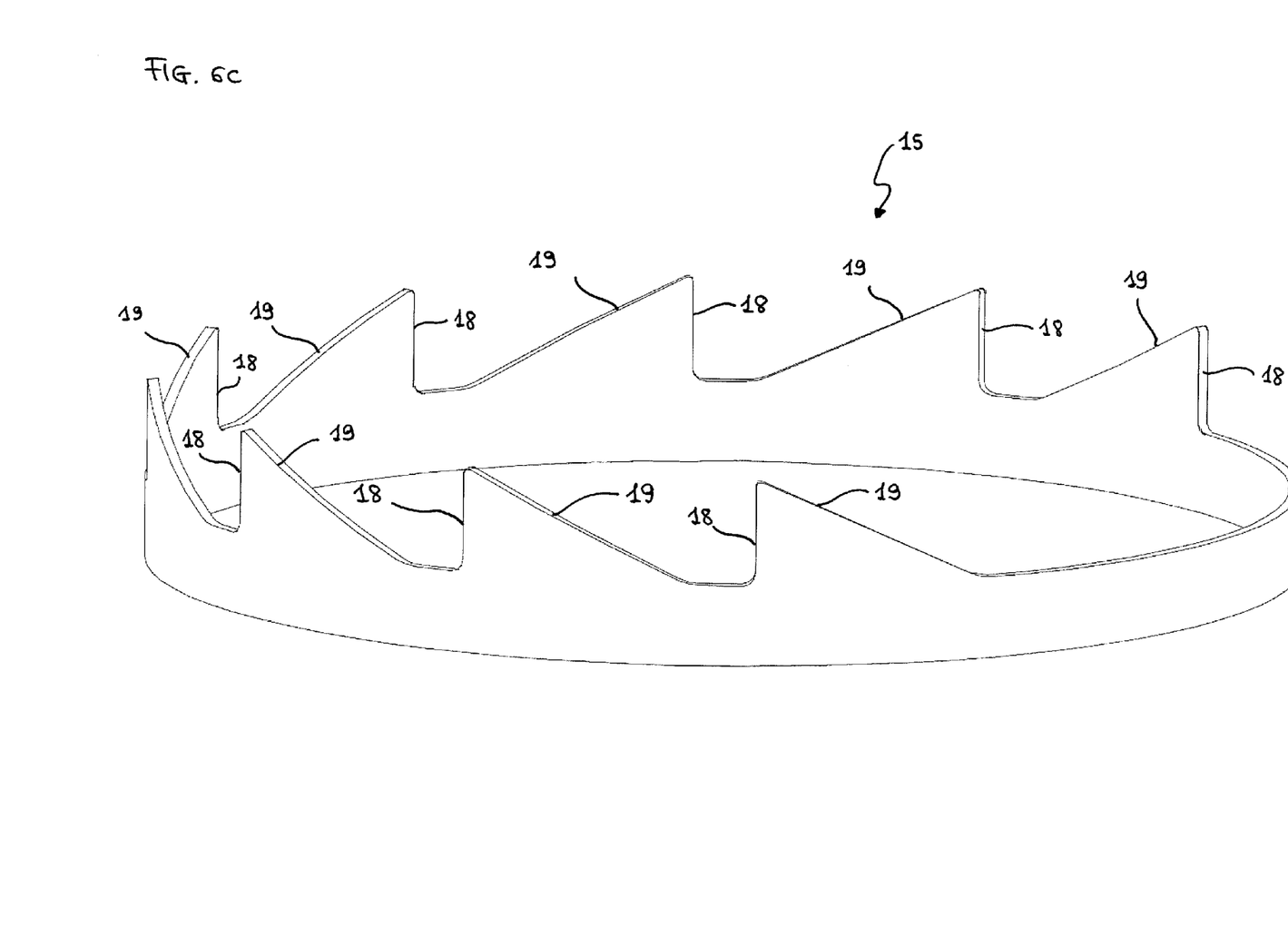

The rotation of the rails 7a, 7b causes the head closure 2a of each line 8 to follow the circumferential path with level differences along the rising sections 18 and descending sections 19. For example, FIGS. 5a and 5b illustrate a head closure 2a descending from a step of the support profile 15. This step determines the separation of the closures 2 of the line 8 during the descent, thus removing the areas of contact between a closure 2 and another. Moreover, as it descends from the step, the head closure 2a partially rotates on itself, causing in turn the rotation of the closure 2 positioned immediately above.

During the rotation, the dispensing means 16 spray the sterilizing substance towards the cavities 5 of the closures 2, so that the internal surfaces of the closures 2 are sterilized. During normal operation, all the internal environment 10 is saturated with a sterilizing substance, so that the external surfaces of the closures 2 are sterilized.

In addition, the separations that are created between the closures 2 during the drop from step and the partial rotations of the closures 2 themselves modify the momentary contact zones between the closures 2.

At the end of a partial or complete revolution of the rotating unit 6, the closures 2 are sent to the outside through an outlet opening 20 formed in the protection casing 9.

When closures 22 of the second format (sport caps) are to be treated, the selector means of the format enable supply of the first channel 13b. The closures 22 of the second format (sport caps) advance by force of gravity in the second conveyor channel 13b and, when passing through the access opening 14, are arranged in the rail 7b of the second type positioned immediately below the access opening 14, thereby forming a first line 8. As mentioned above, each closure 22 is arranged with the cavity 5 facing the protection casing 9. Apart from the above, the functioning is alike to what has been described for the flat caps, but involves the rails 7b of the second type instead of the rails 7a of the first type.

The characteristics of the treatment apparatus of closures for containers with a sterilizing substance, according to the present invention are clear from the foregoing description, as are the resulting advantages.

In particular, with the predisposing of at least two different types of rails, the disclosed treatment apparatus is able to operate on closures of at least two formats (for example threaded caps and sport caps).

If it is necessary to change the format of the closures, it is sufficient to make a selection upstream with the format selecting means, which impose a selection on the treatment apparatus, i.e. enabling supply of the closures of the first format or the closures of the second format and, consequently, the engagement of the rails of the first type or the second type.

Differently to the known solutions, replacements of parts are no longer necessary (for example discs, support receptacles of the caps, chutes, etc.), which involve halting the machine for relatively long times.

Further, the treatment apparatus disclosed herein is structurally simple and compact as the rails of the two different types alternate along the same circumference.

Further, thanks to the presence of a variable-height support profile, the closures are subjected to relative displacements during rotation of the rotating unit. These relative displacements ensure that substantially all the areas are gradually exposed to the treatment of the sterilizing substance. In other words, there are no longer "grey areas" inaccessible to the sterilizing substance, and therefore each closure is sterilized in a more uniform way than in the prior art.

The dimensions of the apparatuses are therefore identical to those of the prior art solutions, effectiveness of the sterilization is increased.

The invention claimed is:

1. A treatment apparatus (1) using a sterilising substance, for closures (2, 22) for containers, comprising:
   a rotating unit (6);
   a plurality of longitudinal rails (7a, 7b) able to house said closures (2, 22) arranged by force of gravity in a same number of lines (8), said plurality of longitudinal rails (7a, 7b) being substantially parallel to one another and being connected to said rotating unit (6) such as to follow a circumferential extension of the rotating unit (6), said plurality of longitudinal rails (7a, 7b) being of at least two types, of which a first type (7a) housing closures (2, 22) of a first closure format (2) and a second type (7b) housing closures (2, 22) of a second closure format (22);
   dispensing means (16) of said sterilizing substance,
   wherein each rail (7a) of the first type alternates with a rail (7b) of the second type along the circumferential extension of said rotating unit (6).

2. The treatment apparatus (1) according to claim 1, wherein the rails (7a) of the first type are configured to house flat caps (2).

3. The treatment apparatus (1) according to claim 1, wherein the rails (7b) of the second type are conformed configured to house sport caps (22).

4. The treatment apparatus (1) according to claim 1, further comprising a protective casing (9) able to define and isolate an internal environment (10).

5. The treatment apparatus (1) according to claim 4, wherein said protective casing (9) comprises walls, said walls being in contact with said internal environment (10).

6. The treatment apparatus (1) according to claim 4, further comprising conveying means (13) for transporting the closures (2, 22) towards said internal environment (10).

7. The treatment apparatus (1) according to claim 6, wherein the conveying means (13) comprise at least a first channel (13a) on which the closures (2) of the first closure format advance by force of gravity and a second channel (13b) on which the closures of the second closure format (22) advance by force of gravity, said protective casing (9) having an access opening (14) into which said first channel (13a) and said second channel (13b) open.

8. The treatment apparatus (1) according to claim 1, further comprising a support profile (15) located at a bottom of said plurality of longitudinal rails (7a, 7b) and also having a circumferential extension such as to support the lines (8) of closures (2, 22).

9. The treatment apparatus (1) according to claim 8, wherein said support profile (15) comprises a top edge with a variable height such that, with the rotating unit (6) in rotating motion, the lines (8) of closures (2, 22) follow a circumferential path with movement up and down and providing relative displacements between the closures (2, 22).

10. The treatment apparatus (1) according to claim 1, wherein said plurality of longitudinal rails (7a, 7b) are parallel to a rotation axis (A) of said rotating unit (6).

11. The treatment apparatus (1) according to claim 10, wherein said rotation axis (A) of the rotating unit (6) is perpendicular or is inclined with respect to a support plane of the treatment apparatus (1).

12. The treatment apparatus (1) according to claim 1, wherein said plurality of longitudinal rails (7a, 7b) are inclined by a predefined angle with respect to a rotation axis (A) of said rotating unit (6).

* * * * *

UNITED STATES PATENT AND TRADEMARK OFFICE
CERTIFICATE OF CORRECTION

PATENT NO. : 9,522,204 B2  
APPLICATION NO. : 14/762154  
DATED : December 20, 2016  
INVENTOR(S) : Paolo Abelli et al.

Page 1 of 1

It is certified that error appears in the above-identified patent and that said Letters Patent is hereby corrected as shown below:

In the Claims

Column 6, Line 51, being Line 14 of Claim 1, after "format (22);" insert --and--.

Column 6, Line 60, being Line 2 of Claim 3, after "type are" delete "conformed".

Signed and Sealed this
Twenty-fifth Day of April, 2017

Michelle K. Lee
*Director of the United States Patent and Trademark Office*